United States Patent
Sember

[11] Patent Number: 6,038,917
[45] Date of Patent: Mar. 21, 2000

[54] METHOD FOR CALCULATING FUEL ECONOMY USING MANIFOLD AIR PRESSURE (MAP) AND FUEL RAIL TEMPERATURE

[75] Inventor: Mark A. Sember, South Lyon, Mich.

[73] Assignee: Chrysler Corporation, Auburn Hills, Mich.

[21] Appl. No.: 08/989,325

[22] Filed: Dec. 11, 1997

[51] Int. Cl.[7] .................................................. G01M 15/00
[52] U.S. Cl. .................................................. 73/114; 73/113
[58] Field of Search .......................... 73/112, 113, 114, 73/116, 117.2, 117.3, 118.1

[56] References Cited

U.S. PATENT DOCUMENTS

| | | | |
|---|---|---|---|
| 4,446,727 | 5/1984 | Kurihara et al. ........................... | 73/113 |
| 4,523,572 | 6/1985 | Staerzl ........................... | 73/114 |
| 4,706,083 | 11/1987 | Baatz et al. ........................... | 73/113 |
| 5,205,160 | 4/1993 | Gandini ........................... | 73/113 |
| 5,427,071 | 6/1995 | Thomas et al. ........................... | 123/491 |
| 5,427,082 | 6/1995 | Thomas et al. ........................... | 123/675 |
| 5,469,826 | 11/1995 | Thomas et al. ........................... | 123/488 |
| 5,492,093 | 2/1996 | Rygiel ........................... | 123/306 |
| 5,535,717 | 7/1996 | Rygiel ........................... | 123/306 |
| 5,584,277 | 12/1996 | Chen et al. ........................... | 123/480 |

*Primary Examiner*—Eric S. McCall
*Attorney, Agent, or Firm*—Mark P. Calcaterra

[57] ABSTRACT

A method for determining an approximate, instantaneous fuel economy of a gasoline powered motor vehicle. The method involves determining a nominal fuel flow through fuel injectors of the vehicle's engine under static pressure conditions and adding to this value a determined additional quantity of fuel flow through the injectors which is caused by dynamic conditions such as engine rpm, vehicle speed, etc. The additional quantity of fuel flow is determined in part by monitoring a pressure drop across the intake manifold of the vehicle. The temperature of the fuel and the octane rating of the fuel are estimated and used to help determine a fuel density value. The fuel density value is then used to determine a total volume of fuel used. The total volume of fuel used is then ratioed with distance information to provide a fuel economy value.

15 Claims, 2 Drawing Sheets

METHOD FOR CALCULATING FUEL ECONOMY USING MANIFOLD AIR PRESSURE (MAP) AND FUEL RAIL TEMPERATURE

BACKGROUND OF THE INVENTION

1. Technical Field

This invention relates to methods for monitoring and determining fuel economy in motor vehicles, and more particularly to a method for monitoring and determining fuel economy of a motor vehicle having a gasoline powered engine.

2. Discussion

Present day motor vehicle such as automobiles, trucks, vans, etc., make use of various methods for determining fuel economy of the vehicle. Some methods even provide an approximation of the instantaneous fuel economy of the vehicle. However, certain drawbacks exist with present day methods for obtaining an average fuel economy.

Most present day methods for obtaining an average fuel economy typically make use of algorithms which utilize fuel-used estimations. The fuel-used estimations are based on the accumulated time which each fuel injector of the engine of the vehicle is turned on. The injectors are further assumed to be operating under static pressure conditions, that is, conditions which do not result in an appreciable change in the amount of fuel flowing through the injectors. Thus, various factors such as wind resistance encountered by the vehicle, the road the vehicle is traveling on, vehicle speed, engine rpm, fuel temperature, fuel octane, etc., are not taken into account by previously developed fuel economy estimation methods. Thus, current approaches for estimating fuel economy do not take into account the various dynamic variables that can significantly influence the vehicle's fuel economy. This can result in a significant degree of error, sometimes as much as 10% or greater, in the estimated fuel economy of the vehicle.

Accordingly, it would be highly desirable to provide a method for more accurately determining the fuel economy of a gasoline powered motor vehicle. More specifically, it would be highly desirable to provide a method for taking into account the numerous dynamic variables such as engine rpm, vehicle speed, fuel temperature, fuel octane and other variables which have a definite influence on the instantaneous fuel economy of the vehicle. It would further be desirable if such a method could be provided which enables the above-mentioned variables to be taken into account while providing an accurate fuel economy value, in real time, such that a driver or operator of a vehicle can monitor the instantaneous fuel economy of the vehicle.

SUMMARY OF THE INVENTION

The above features are provided by a method for calculating fuel economy in accordance with the preferred embodiments of the present invention. In one preferred embodiment the method involves the steps of determining a nominal fuel flow through the injectors of the engine under static pressure conditions and determining an additional quantity of fuel flow through the injectors, in part by monitoring a pressure drop across an intake manifold of the vehicle's engine, to account for dynamic pressure transients which cause an increase in the fuel flow through the injectors. A total mass quantity of fuel used for a given period of time is then determined by adding the nominal fuel flow value with the additional fuel flow value to provide a total mass fuel used value. This value is then converted to a total fuel used volume value which is used to determine an instantaneous fuel economy value. In this manner, various dynamic conditions such as engine rpm, vehicle speed and other variables which affect the quantity of fuel used by the engine can be taken into account in determining a fuel economy value. Accordingly, an even more accurate determination of instantaneous fuel economy can be obtained.

In the preferred embodiment described above, the step of converting the total mass fuel used value to a total fuel used volume value includes the steps of taking into account the temperature of the fuel flowing through the injectors of the engine. This is accomplished by estimating the temperature of the fuel based on the temperature of the coolant flowing through the engine. The fuel supplied to the injectors is supplied through a fuel rail typically mounted on top of the engine. Since the temperature of the fuel rail, and thus the fuel flowing therethrough, is generally understood to track the temperature of the coolant flowing through the engine, a close estimation of the fuel temperature can be obtained. Similarly, an average octane value can be determined and used together with the estimated fuel temperature to provide an estimated fuel density. The estimated fuel density can then be used in converting the total mass quantity of fuel used by the injectors over a short time interval into a total fuel used volume value.

DETAILED DESCRIPTION OF THE PREFERRED EMBODIMENT

Figure 1A:
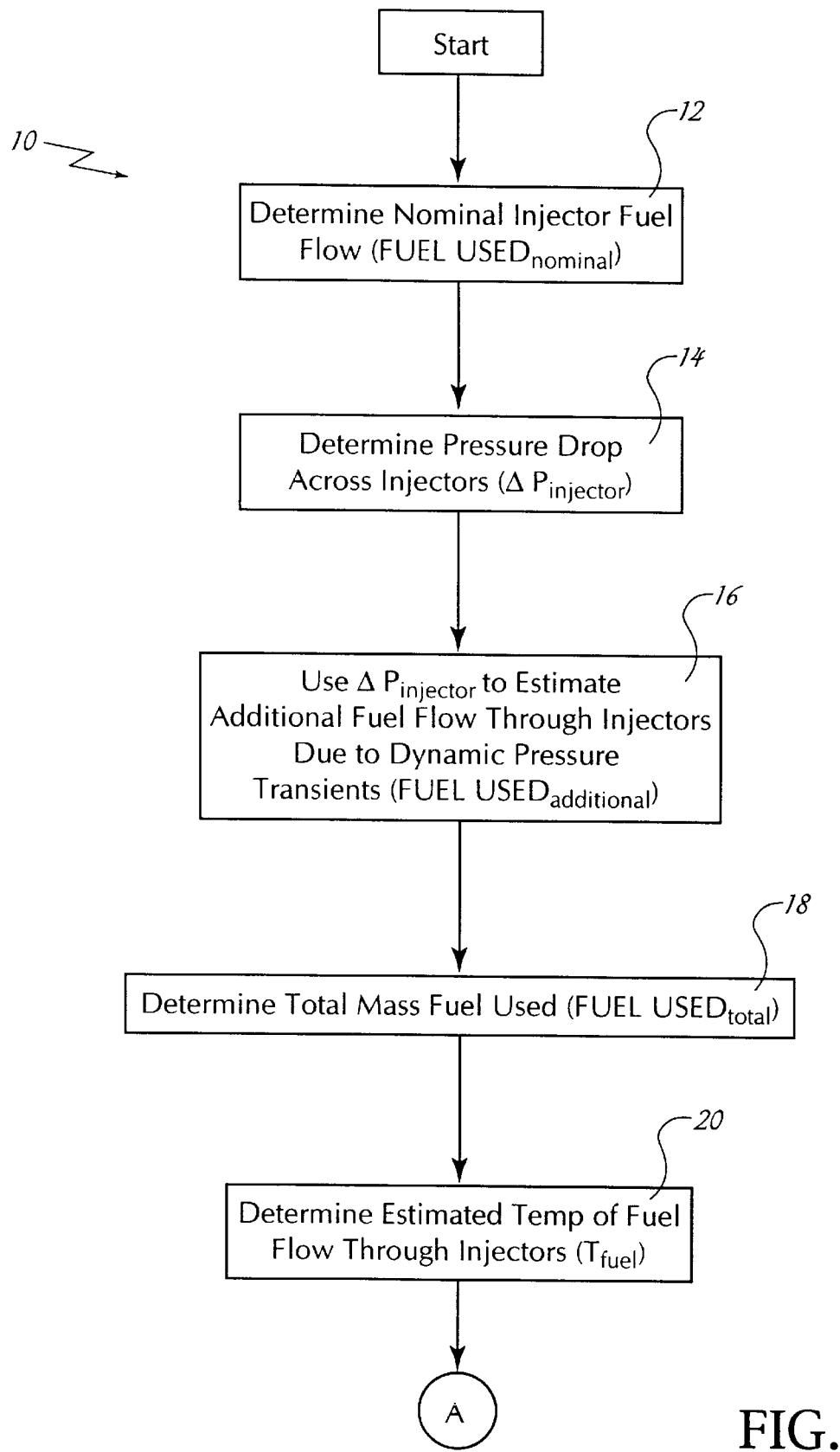
FIGS. 1A and 1B represent a flow chart setting forth the basic steps of the method of the present invention.
Figure 1B:
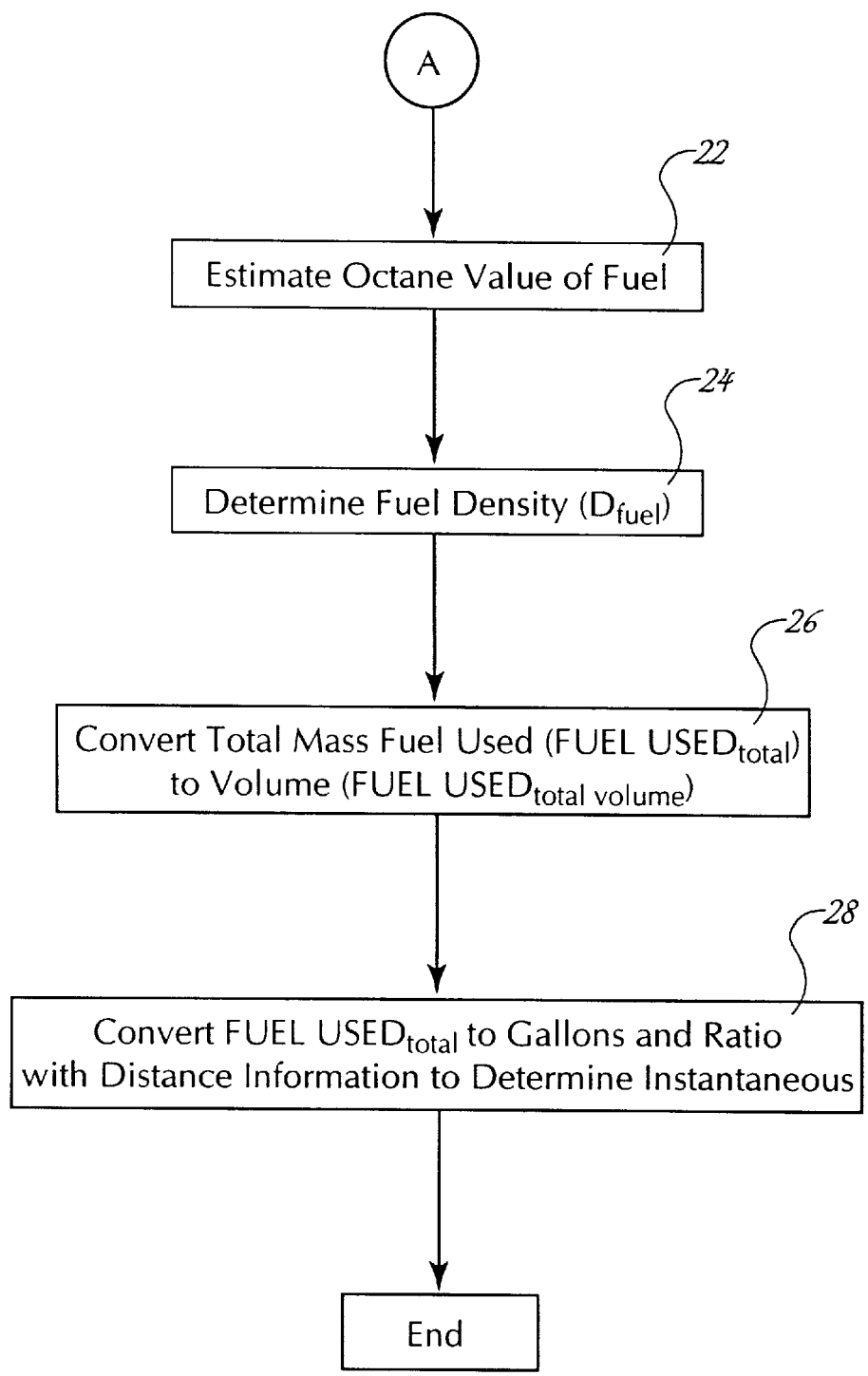

Referring to FIG. 1, there is shown a flow chart of a method 10 in accordance with a preferred embodiment of the present invention for estimating a fuel economy value for a gasoline powered motor vehicle. It will be appreciated immediately that the method of the present intention is applicable to a wide variety of motor vehicles having gasoline powered engines. While it is anticipated that the present invention will find particular utility in connection with automotive cars and trucks, the method is also well suited to any gasoline powered vehicle where it is desirable to monitor the vehicle's fuel economy and to provide an indication of the instantaneous fuel economy of the vehicle to an operator.

The method 10 initially involves determining a nominal injector fuel flow (FUEL USED$_{nominal}$), as indicated at step 12. This is determined empirically and represents the amount of fuel that the injectors of the gasoline powered engine would flow under static and nominal pressure conditions. Next, steps 14 and 16 are performed to determine an additional quantity of fuel used (FUEL USED$_{additional}$) by the engine of the vehicle due to dynamic conditions such as engine rpm, vehicle speed, etc. This is first performed, at step 14, by determining a pressure drop across the injectors ($\Delta P_{injector}$). This is accomplished by the following formula:

$$\Delta P_{injector} = \text{Fuel Rail}_{rel} + \text{Barometric}_{abs} - MAP_{abs} (\text{KPa})$$

where $\Delta P_{injector}$ is the total pressure drop (static and dynamic) across the injectors;

Fuel Rail$_{rel}$ is the pressure of the fuel rail which supplies fuel to the injectors, which is assumed to be static relative to barometric pressure;

Barometric$_{abs}$ is absolute barometric pressure; and $MAP_{abs}$(KPa) is the pressure drop across the intake manifold of the engine measured in real time and averaged over a 10 millisecond window.

Step 16 of the method is accomplished by the following formula:

$$FUEL\ USED_{additional} = \Delta P_{injector} \times C_{fp} \cdot FUEL\ USED_{nominal}(mg)$$

where:

$FUEL\ USED_{additional}$ is the additional amount of fuel used because of dynamic transients experienced by the vehicle's engine; and $C_{fp}$ equals a correction factor ($1.25 \times 10^{-3}$/KPa).

Once the additional quantity of fuel used ($FUEL\ USED_{additional}$) is determined, the total fuel used by the injectors over a given period of time is determined, as indicated at step 18, by the following formula:

$$FUEL\ USED_{total} = FUEL\ USED_{nominal} + FUEL\ USED_{additional}(mg)$$

This determination represents the total mass quantity of fuel used ($FUEL\ USED_{total}$) over a given period of time. Additionally, this value also takes into account dynamic and rapid fluxuations in the intake manifold air pressure (MAP) during acceleration events, as well as compensating for barometric pressure changes at every ignition "on" event of the vehicle's engine.

Referring further to FIG. 1A, the next step is to estimate the temperature of fuel flowing through the injectors ($T_{fuel}$) as indicated at step 20. This is accomplished by first assuming that the external portion of the fuel rail which supplies fuel to the injectors will track the temperature of the engine coolant flowing through the engine, with a constant offset, under highway driving conditions. Making the assumption that the fuel contained in the fuel rail has reached thermal equilibrium within the external portion of the fuel rail, then the temperature of the fuel can be determined by the following formula:

$$T_{fuel} = T_{coolant} - T_{offset}(°C.)$$

where:

$T_{coolant}$ is measured in real time; and $T_{offset}$ is an empirically derived value of 40° C.

The next step, step 22, involves estimating the octane value of the fuel being used. Since the range of fuel octanes available to a consumer is most commonly between 87 to 93, using the (R+M)/2 method a 90 octane fuel is derived. The density for a theoretical 90 octane fuel can be derived by the following formula:

$$(D_{87(10°\ C.)} + D_{93(10°\ C.)})/2 = D_{90(10°\ C.)}(mg/mL)$$

In the above formula $D_{90(10°\ C.)}$ is equal to 755 mg/mL and is a mean octane density value created to minimize the error generated by the available range of fuel octanes. The values $D_{87(10°\ C.)}$ and $D_{93(10°\ C.)}$ are obtained from tables for a temperature of 10° C.

Referring further to FIG. 1, as indicated at step 24, the fuel density ($D_{fuel}$) is now determined. The fuel density can be represented by the following formula:

$$D_{fuel} = D_{90(10°\ C.)} \cdot (1 + Vxc(10°\ C. - T_{fuel}))^{-1}$$

Vxc represents the volume expansion coefficient of gasoline at $1 \times 10^{-3}$/°C.). This equation dynamically calculates a density for the fuel as a function of the temperature of the engine coolant. Utilizing the engine coolant temperature as a reference for the fuel temperature enables the method of the present invention to adjust for the vast temperature extremes found throughout the world.

With continuing reference to FIG. 1, at step 26 the total mass fuel used ($FUEL\ USED_{total}$) is converted to a total fuel used volume value ($FUEL\ USED_{volume}$). This is accomplished by the following formula:

$$FUEL\ USED_{volume} = FUEL\ USED_{total}/D_{fuel}(mL)$$

Lastly, at step 28, $FUEL\ USED_{volume}$ is converted to gallons and ratioed with distance information in the form of distance pulses from the vehicle's engine control module. The distance pulses represent the distance increments that the vehicle has traveled during each measurement period. In this manner a miles-per-gallon fuel economy value is obtained. This fuel economy value can be displayed to an operator of a vehicle via a wide range of displays such as an LED display, an LCD display, etc.

The method of the present invention therefore allows variations in the fuel economy calculation which are due to vehicle speed and engine rpm to be accounted for by monitoring the manifold air pressure, the barometric pressure and using the empirically determined correction factor ($C_{fp}$) to take into account the effect vehicle speed and engine rpm have on the fuel flowing through the injectors. This additional amount of fuel used ($FUEL\ USED_{additional}$), which is based on dynamic pressure transients, is then added to the nominal amount of fuel used ($FUEL\ USED_{nominal}$). The resulting value thus corrects for a new barometric pressure at every injector "on" event.

The method of the present invention further takes into account variations in the fuel economy calculations which would otherwise be caused by variations in the fuel temperature. These variations are accounted for by utilizing the engine coolant temperature and an empirically derived offset temperature (i.e., $T_{offset}$) to obtain a fuel temperature estimate which is then used in dynamically calculating fuel density. This, in turn, enables the total volume of fuel used ($FUEL\ USED_{volume}$) over a given time to be calculated more accurately than with previously developed methods of determining fuel economy.

Lastly, variations in fuel economy calculations which are caused by unknown fuel octanes are taken into account with the method of the present invention by creating a median fuel octane value. This median fuel octane value is then utilized to obtain a median fuel density value at a predetermined temperature (i.e., 10° C.). In this manner the density of the fuel, and therefore the total volume of fuel used, can be determined even more accurately than with previously developed fuel economy methods. The method of the present invention reduces the error between the calculated fuel economy and actual fuel economy from approximately 10% or higher to approximately 2% or less.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

We claim:

1. A method for determining a fuel economy of a gasoline powered motor vehicle having an engine, a plurality of fuel injectors and an intake manifold, said method comprising the steps of:

determining a nominal fuel flow through said fuel injectors under static pressure conditions;

determining an additional quantity of fuel flow through said fuel injectors caused by dynamic pressure transients by determining a pressure drop across said intake manifold;

determining a total mass quantity of fuel used for a given period of time by adding said determined nominal fuel flow to said additional quantity of fuel flow to produce a total mass fuel used value;

converting said total mass fuel used value to a total fuel used volume value by using an estimated octane value for said fuel and a density of said fuel which is determined by estimating a temperature of said fuel flowing through said injectors based on a temperature of coolant flowing through said engine; and using said total fuel used volume value to determine an instantaneous fuel economy value.

2. The method of claim 1, wherein said step of determining said additional quantity of fuel flow comprises the step of determining a change in pressure across at least one of said fuel injectors.

3. The method of claim 2, wherein the step of determining a change in pressure across one of said injectors is determined in accordance with a formula comprising:

$$\Delta P_{injector} = \text{Fuel Rail}_{ref} + \text{Barometric}_{abs} - MAP_{abs} (\text{KPa})$$

where:

$\Delta P_{injector}$ represents the change in pressure across a single injector;

Fuel Rail$_{rel}$ represents a predetermined static fuel rail pressure;

Barometric$_{abs}$ represents measured absolute barometric pressure;

$MAP_{abs}$ represents absolute manifold air pressure measured in real time and averaged over a 10 ms window.

4. The method of claim 3, wherein the step of determining said additional quantity of fuel flow through said fuel injectors is performed in accordance with a formula comprising:

$$\text{FUEL USED}_{additional} = \Delta P_{injector} \cdot C_{fp} \cdot \text{FUEL USED}_{nominal} (\text{mg})$$

where:

$C_{fp}$ represents a correction factor for pressure ($1.25 \times 10^{-3}$/KPa); and FUEL USED$_{nominal}$ is the amount of fuel said injectors flow under static pressure conditions.

5. The method of claim 4, wherein the step of determining said total mass quantity of fuel used is determined in accordance with a formula comprising:

$$\text{FUEL USED}_{total} = \text{FUEL USED}_{nominal} + \text{FUEL USED}_{additional} (\text{mg}).$$

6. The method of claim 1, wherein the step of determining said temperature of said fuel flowing through said injectors is accomplished by a formula comprising:

$$T_{fuel} = T_{coolant} - T_{offset} (°C.)$$

where:

$T_{fuel}$ comprises the estimated temperature of said fuel flowing through said injector;

$T_{coolant}$ comprises the temperature of said coolant flowing through said engine;

$T_{offset}(°C.)$ comprises a constant offset equal to approximately 40° C.

7. The method of claim 6, wherein the step of determining said density of said fuel is accomplished by a formula comprising:

$$D_{fuel} = D_{90(10° C.)} \cdot (1 + Vxc(10° C. - T_{fuel}))^{-1}$$

where:

$D_{fuel}$ comprises the density of said fuel;

$D_{90(10° C.)}$ comprises the density for a theoretical 90 octane fuel;

Vxc comprises the volume expansion coefficient of gasoline (at $1 \times 10^{-3/°}$C.).

8. A method for determining a fuel economy of a gasoline powered motor vehicle having an engine including a plurality of fuel injectors, an intake manifold and an engine coolant circulating within said engine, said method comprising the steps of:

determining a nominal fuel flow through said injectors under static pressure conditions;

monitoring air pressure across said intake manifold and using said monitored air pressure to determine a total change in pressure across one of said injectors;

using said total change in pressure across one of said injectors and said nominal fuel flow through said injectors to determine an additional fuel flow through said injectors caused by dynamic pressure transients;

determining a total mass fuel flow through said injectors based on said nominal fuel flow and said additional fuel flow;

converting said total mass fuel flow through said injectors into a total fuel used volume value; and using said total fuel used volume value to determine an instantaneous fuel economy value.

9. The method of claim 8, wherein the step of converting said total mass fuel flow to a total fuel used volume value comprises the step of:

estimating a temperature of said fuel flowing through said injectors based on a measured temperature of said coolant circulating through said engine.

10. The method of claim 8, wherein said step of converting said total mass fuel flow to a total fuel used volume value comprises the step of:

determining an average octane value for said fuel.

11. The method of claim 8, wherein the step of converting said total mass fuel flow to a total fuel used volume value comprises the steps of:

determining an average octane value for said fuel;

estimating a temperature of said fuel flowing through said injectors based on a temperature of said coolant flowing through said engine;

applying a constant to said estimated temperature of said fuel flowing through said injectors;

determining a volume expansion coefficient of said fuel; and using said estimated temperature of said fuel, said average octane value and said volume expansion coefficient of said fuel to determine a density of said fuel.

12. The method of claim 10, wherein said step of converting said total mass fuel flow to a total fuel used volume value further comprises the step of:

using said density of said fuel and said total mass fuel flow used to determine said total fuel used volume value.

13. A method for determining an instantaneous fuel economy for a gasoline powered motor vehicle having an engine, wherein said engine has coolant circulating therethrough, a fuel rail for supplying fuel to a plurality of fuel injectors, and an intake manifold, said method comprising the steps of:

determining a nominal fuel flow through said injectors over a given time interval;

determining an additional fuel flow through said injectors over said time interval caused by dynamic conditions associated with the operation of said engine by the steps including:

monitoring manifold air pressure;

monitoring barometric air pressure;

determining a pressure drop across said fuel rail;

using said manifold air pressure, said barometric air pressure and said fuel rail pressure to determine a pressure drop across one of said injectors; and using said pressure drop across said one injector and said nominal fuel flow through said injectors to generate a value for said additional fuel flow through said injectors;

using said value for said additional fuel flow through said injectors and said nominal fuel flow through said injectors to determine a total mass fuel flow value through said injectors;

converting said total mass fuel flow value through said injectors into an equivalent volume value; and using said volume value to determine a fuel economy value.

14. The method of claim 12, wherein said step of converting said total mass fuel flow value into said equivalent volume value comprises the steps of:

estimating a temperature of said fuel flowing through said injectors based on an estimate of a temperature of said coolant flowing through said engine;

estimating an octane value for said fuel;

using said octane value and said estimated temperature of said fuel to determine a density of said fuel; and using said total mass fuel flow value and said density of said fuel to determine said equivalent volume value.

15. The method of claim 13, wherein the step of determining a density for said fuel further comprises the step of determining a volume expansion coefficient of said fuel.

* * * * *